United States Patent
Ghalili et al.

(10) Patent No.: US 12,390,560 B2
(45) Date of Patent: Aug. 19, 2025

(54) EXOSOME BONE GRAFT SYSTEMS, PRODUCTS AND METHODS

(71) Applicants: Babak Ghalili, New York, NY (US); Keyon Janani, Baton Rouge, LA (US); Peter Scherp, Denham Springs, LA (US); John Borja, Keyport, NJ (US)

(72) Inventors: Babak Ghalili, New York, NY (US); Keyon Janani, Baton Rouge, LA (US); Peter Scherp, Denham Springs, LA (US); John Borja, Keyport, NJ (US)

( * ) Notice: Subject to any disclaimer, the term of this patent is extended or adjusted under 35 U.S.C. 154(b) by 597 days.

(21) Appl. No.: 17/948,666

(22) Filed: Sep. 20, 2022

(65) Prior Publication Data

US 2023/0089252 A1    Mar. 23, 2023

Related U.S. Application Data

(60) Provisional application No. 63/246,930, filed on Sep. 22, 2021.

(51) Int. Cl.
*A61L 27/54* (2006.01)
*A61L 27/36* (2006.01)

(52) U.S. Cl.
CPC .......... *A61L 27/54* (2013.01); *A61L 27/3608* (2013.01); *A61L 27/365* (2013.01); *A61L 2430/02* (2013.01)

(58) Field of Classification Search
None
See application file for complete search history.

(56) References Cited

U.S. PATENT DOCUMENTS

| | | |
|---|---|---|
| 11,116,872 B2 | 9/2021 | Ganey et al. |
| 2014/0308217 A1 | 10/2014 | Schaeffer-Korbylo et al. |
| 2015/0023908 A1 | 1/2015 | Al-Qahtani |
| 2020/0230174 A1 | 7/2020 | Chung et al. |

FOREIGN PATENT DOCUMENTS

| | | |
|---|---|---|
| WO | 2020223349 A1 | 11/2020 |
| WO | 2021062084 A1 | 4/2021 |
| WO | 2022150734 A1 | 7/2022 |

OTHER PUBLICATIONS

United Kingdom Intellectual Property Office, Examination Report under Section 18(3), Application No. GB2404047.9, Mailed Apr. 28, 2025, 6 pages.

Burke et al, "Stem Cell-Derived Exosomes: A Potential Alternative Therapeutic Agent in Orthopaedics", Stem Cells International, pp. 1-6, Article ID 5802529, http://dx.doi.org/10.1155/2016/5802526, 2016, 6 pages.

Keshtkar et al, "Mesenchymal stem cell-derived extracellular vesicles: novel frontiers in regenerative medicine", Stem Cell Research & Therapy, pp. 1-9, https://doi.org/10.1186/s13287-018-0791-7, 2018, 9 pages.

Phinney et al, "Concise Review: MSC-Derived Exosomes for Cell-Free Therapy", Tissue-Specific Stem Cells, pp. 851-858, Published Mar. 7, 2017, 8 pages.

Taghizadeh et al, "Towards Clinical Applications of Umbilical Cord Derived Mesenchymal Stem Cells", Perinatal Stem Cells, pp. 347-359 , DOI: 10.1007/978-1-4939-1118-9_31 , 2014, 13 pages.

Zhang et al, "Exosomes: biogenesis, biologic function and clinical potential", Cell & Bioscience, pp. 1-18, https://doi.org/10.1186/s13578-019-0282-2, 2019, 18 pages.

Chen et al., "Exosomes derived from miR-375-overexpressing human adipose mesenchymal stem cells promote bone regeneration" Cell Proliferation, 2019, vol. 52, Issue 5, DOI: 10.1111/cpr.12669, 14 pages.

Teotia et al., "Exosime-Functionalized Ceramic Bone Substittue Promotes Critical-Sized Bone Defect Repair in Rats" ACS Applied Bio Materials, Apr. 7, 2021, vol. 4, Issue 4, httpsL//doi.org/10.1021/acsabm.lc00311, 11 pages.

United States Patent and Trademark Office, International Search Report, Application No. PCT/US2022/044102, mailed Jan. 18, 2023, 3 pages.

United States Patent and Trademark Office, Written Opinion of the International Searcing Authority, Application No. PCT/US2022/044102, mailed Jan. 18, 2023, 5 pages.

Yang et al. "Integration of Human Umbilical Cord Mesenchymal Stem Cells-Derived Exosomes with Hydroxyapatite-Embedded Hyaluronic Acid-Alginate Hydrogel for Bone Regeneration" ACS Biomaterials Science & Engineering, Feb. 6, 2020, vol. 6, Iss. 3. https://dx.doi.org/10.1021/acsbiomaterials.9b01363, 13 pages.

*Primary Examiner* — Michael V Meller
(74) *Attorney, Agent, or Firm* — ZIEGLER IP LAW GROUP, LLC.

(57) ABSTRACT

The present disclosure relates to exosome bone graft systems and compositions and preservative systems and compositions as well as methods of use and methods of manufacturing of them.

9 Claims, 3 Drawing Sheets

EXOSOME BONE GRAFT SYSTEMS, PRODUCTS AND METHODS

FIELD

The aspects of the present disclosure relate to exosome bone graft systems and products as well as methods of making and using same.

BACKGROUND

Exosomes are vesicles secreted by many cell types. They have a bi-lipid membrane and can be about 30 to about 100 nm in size. Exosomes are of endocytic origin and are normally released by the cells in which they are formed into the extracellular environment. They can contain various cellular products such as lipids, proteins and genetic materials that are being discarded by the cells in which they are created.

Exosomes are fragile vesicles and maintaining their integrity in a suitable environment is necessary so that they can be utilized in difficult therapeutic compositions.

A bone graft is a surgical procedure used to fix problems with bones or joints.

Bone grafting, or transplanting of bone tissue, is beneficial in fixing bones that are damaged from trauma or problem joints. It's also useful for growing bone around an implanted device, such as a total knee replacement where there is bone loss or a fracture. A bone graft may fill an area where bone is absent or help provide structural stability. The bone used in a bone graft can come from your body or a donor, or it can be entirely synthetic. It can provide a framework where new, living bone can grow if it's accepted by the body.

Bone grafting is done for numerous reasons, including injury and disease. There are four main reasons bone grafts are used. A bone graft may be used in the case of multiple or complex fractures or those that don't heal well after initial treatment. Fusion helps two bones heal together across a diseased joint. Fusion can be done on the spine. Regeneration is used for bone lost to disease, infection, or injury. This can involve using small amounts of bone in bone cavities or large sections of bones. A graft can be used to help bone heal around surgically implanted devices, like joint replacements, plates, or screws.

Bone grafts can be used in dental practice, for example, in periodontal procedures as well as in orthopedic practice, for example, in spine, hip and knee surgeries. The grafting materials that can be natural bone material from various sources or man-made material can create a framework for new bone growth while the physical properties of the graft material can be used to maintain separation of other tissues. The natural bone material used for the grafts can be fresh or frozen, freeze-dried or demineralized freeze-dried. The grafting materials can be material derived from bone material such as, for example, cadaveric sources (allograft), derived from animal sources (xenograft) or derived from the patient (autogenous) or derived from non-bone, but otherwise natural or man-made sources (alloplast).

BRIEF DESCRIPTION OF THE DRAWINGS

The accompanying drawings illustrate presently preferred embodiments of the present disclosure, and together with the general description given above and the detailed description given below, serve to explain the principles of the present disclosure.

SUMMARY

In one embodiment, a bone graft material is provided. The bone graft material includes an exosome mixture including a plurality of exosomes; dimethyl sulfoxide; and epsilon poly L-lysine; and one or more natural bone materials, one or more man-made substitute bone materials or a combination thereof.

In another embodiment, a bone graft material is provided. The bone graft material includes an exosome mixture including a plurality of exosomes; a plurality of liposomes; dimethyl sulfoxide; and epsilon poly L-lysine; and one or more natural bone materials, one or more man-made substitute bone materials or a combination thereof.

In another embodiment, a method for bone regeneration is provided. The method for bone regeneration includes using a bone graft material, including an exosome mixture including a plurality of exosomes; dimethyl sulfoxide; and epsilon poly L-lysine, and one or more natural bone materials, one or more man-made substitute bone materials or a combination thereof; and applying the bone graft material to an area of bone tissue, one of more areas adjacent bone tissue or both where bone growth is desired.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The term "topically acceptable" means the compound, substance or device may be administered to or onto the surface of a patient, including the skin or other accessible tissues, without substantial harmful effects to the body part and/or its surfaces.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

All of the embodiments included here are with the proviso that the sum of ingredients in the exemplary compositions does not exceed 100%.

The aspects of the present disclosure relate to exosome mixtures, systems and compositions and preservative systems and compositions and methods of forming them in which the viable (i.e., active) structure and integrity of the exosomes and its contents can be maintained using additional components to preservative the exosomes to deter disadvantageous occurrences such as, for example, clumping. Aspects of the present disclosure also include fluid mixtures and compositions of exosomes and exosome mixtures including liposomes and both also include additional components to preservative and maintain the structure and integrity of the exosomes and its contents and the liposomes as well as prevent deleterious conditions such as, for example, clumping of the exosomes. Aspects of the present disclosure also include bone graft therapeutic compositions including a combination of bone or other material to be used for bone grafts and exosome mixture embodiments of the present disclosure as well as the methods of making and using/treating using such bone graft therapeutic compositions.

A "liposome" is a generic term encompassing a variety of single and multilamellar lipid vehicles formed by generating enclosed lipid bilayers or aggregates. Liposomes may have vesicular structures with a bilayer membrane, generally comprising a phospholipid, and an inner medium that generally comprises an aqueous composition. Liposomes for the present disclosure may include unilamellar liposomes, multilamellar liposomes, and multivesicular liposomes and may be positively charged, negatively charged, or neutrally charged.

The exosomes included in exosome mixture embodiments of the present disclosure can be obtained or extracted from different sources including various cell types, for example, placental cells and stem cells. The exosomes from stem cells contain biomolecules that are different from the exosomes of other cells. Exosomes from urine, blood or plasma serum, or epithelial cells or differentiated cells, will not have the same regenerative effect as compared to stem cell exosomes (e.g., mesenchymal stem cells (MSCs) exosomes). Exosomes are generated by all living cells. The contents of stem cell exosomes (e.g., MSC exosomes) is dependent on where they are coming from. Stem cells have a certain regenerative effect when injected. These effects can be replicated by using exosomes from stem cells. The regenerative effect of stem cells likely comes from the exosome itself and its contents. Mesenchymal stem cell exosomes transfer functional cargos like miRNA and mRNA molecules, peptides, proteins, cytokines and lipids from MSCs to the recipient cells. These exosomes participate in intercellular communication events and contribute to the healing of injured or diseased tissues and organs. and, as a result, can be more beneficial. Exosome extraction can be performed using different known types of centrifugation and ultracentrifugation. After the centrifugation and ultracentrifugation steps, they can be further purified using additional known procedures including, for example, gel filtration. Exosomes can be present in embodiments of the exosome mixtures of the present disclosure in an amount of about 0.25 wt % to about 1.00 wt %, about 0.50 wt % or about 10 million to about 20 trillion exosomes, or about 1 billion exosomes per 1 ml volume in the exosome mixture.

While all mammalian cells secrete exosomes, only exosomes derived from stem cells are currently considered therapeutic. Stem cells can be cultured in many different ways. This includes 2D culturing, which typically occurs in flasks or cylinders. Three dimensional culturing is facilitated in bioreactors, which can include stirred tank and hollow fiber setups. Independent of the culturing method in which they are propagated of the stem cell culture, the exosomes are secreted into the culture medium by the stem cells. The culturing method can determine the concentration of exosomes per volume culture medium.

In order to isolate stem cell derived exosomes, the conditioned culture medium undergoes a procedure that concentrates the exosomes and ultimately removes the culture medium which then can be replaced with the desired medium for various pharmaceutical and/or cosmetic compositions and uses, e.g., 0.9 wt % sodium chloride or phosphate buffered saline for other applications such as cosmetics. The methods for exosome isolation include but are not limited to the following:

1. Ultracentrifugation a. Conditioned medium is centrifuged at lower speeds to remove cell debris.

b. Then, the remaining supernatant is centrifuged at high g forces (e.g., 100,000× g) to facilitate the sedimentation of the exosomes.

c. Exosome pellets are then washed and resuspended in the desired medium.

2. Sucrose Density Centrifugation a. Exosomes are separated in a density gradient established by different sucrose concentrations.

b. The exosome fraction is then isolated and further processed by washing and resuspension in the desired medium.

3. Size Exclusion Chromatography a. Conditioned medium is loaded onto a column that allows for the separation of exosomes from other particles based on their size.

4. Precipitation a. Conditioned medium is exposed to agents that lower the solubility of exosomes and thereby facilitate their precipitation.
b. This agent can be polyethylene glycol (PEG) or other suitable polymers or compounds.
c. Exosomes are then washed and can be resuspended in the medium of choice.

5. Tangential Flow Filtration/Ultrafiltration a. Conditioned medium is filtered using tangential flow filters.
b. Exosomes are retained in the filter (retentate)
c. The exosomes are washed while conditioned medium is removed.
d. Exosomes are suspended in the medium of choice.

6. Immunoprecipitation a. Exosomes are precipitated from conditioned medium using antibodies targeted to specific exosome proteins.
b. Exosomes are then released, washed, and resuspended in desired medium.

7. Immunoaffinity/With or Without Chromatography a. Exosomes are retained on a column or other physical support by antibodies that are targeted to unique exosome proteins.
b. Exosomes are then washed, released from support, and resuspended in desired medium.

8. Flow-Field Flow Fractionation a. Originated as a detection method for exosome populations, it has been recently used to isolate exosomes from conditioned medium.

Liposomes included in the exosome mixtures of the present disclosure are lipid vessel that can contain stabilizing agents, preservatives, and penetration enhancers. Such liposomes have at least one lipid bilayer and can be formed, for example, using lecithin without the use of ethanol or other alcohol because of the latter's adverse effects on exosomes. Other than lecithin (phospholipid aka. phosphatidylcholine), other examples of lipids that can be used to form liposomes used in embodiments of the present disclosure are phosphatidic acid (phosphatidate) (PA) phosphatidylethanolamine (cephalin) (PE), phosphatidylserine (PS), phosphatidylinositol (PI), phosphatidylinositol phosphate (PIP), phosphatidylinositol bisphosphate (PIP2) and phosphatidylinositol trisphosphate (PIP3), phosphosphingolipids, peramide phosphorylcholine (Sphingomyelin) (SPH), ceramide phosphorylethanolamine (Sphingomyelin) (Cer-PE), ceramide phosphoryllipid etc. Additionally, niosomes can also be used in place or in combination with liposomes even though niosomes may not as stable as liposomes Niosomes are vesicles composed of hydrated non-ionic surfactants, such as alkyl-ether, esters, and amides, and cholesterol and can be used as an alternative to liposomes. Niosomes can be made using the same process as is used in making liposomes.

The liposomes used in embodiments of the exosome mixtures of the present disclosure can be present in embodiments in an amount of about 1.00 wt % to about 20.00 wt %, about 5.0 wt % to about 15 wt %, about 10 wt %.

Embodiments of the present disclosure include mixtures where the exosomes are located outside the liposome, as well as mixtures where the exosomes are located inside the liposome or a mixture of the two.

The compositions with exosome mixtures and optionally and preferably with liposomes of the present disclosure, additional components are added to the mixture, for example, to preservative and maintain the structure and integrity of the exosomes and its contents as well as other benefits. When exosomes disintegrate, they will release their contents and are no longer able to fuse with a living cell. Most released bio compounds will degrade fast, but some proteins may still be able to fulfill their biological function. The additional components can include, for example, dimethyl sulfoxide (DMSO) as well as at least one or more typical preservative compounds including for example: epsilon poly L-lysine, "Linatural," phenoxyethanol, and quaternary ammonium cations, such as, for example, benzalkonium chloride. The pH of the resulting exosome mixtures of the present disclosure can be between about 5 and about 7.5, which is a critical range in which the exosomes should reside. The pH can be adjusted to be within this range using buffers such as ammonium sulfate, sodium citrate, sodium chloride, sodium acetate.

The resulting exosome mixtures including exosome, optionally including liposome and/or niosomes and additional components (e.g., DMSO) and a preservative (e.g., epsilon poly L-lysine)) can be maintained for storage prior to use at a temperature of from about −200° C. to about room temperature (about 25° C.). The exosome mixtures, DMSO and preservative (e.g., epsilon poly L-lysine) composition, optionally including liposomes, embodiments of the present disclosure could maintain the structure and integrity of the exosomes for a time period for as much as two years at a temperature of at most about 4.4° C.

DMSO is a polar aprotic solvent that is preferably included in exosome mixture embodiments of the present disclosure and can deter the presence of clumping of the exosomes as well as act as a solvent/skin penetrant in embodiments of the present disclosure. DMSO can be present in exosome mixture embodiments of the present disclosure in an amount of about 0.001 wt % to about 0.50 wt %, but no more. Other examples of compositions in place of or in combination with DMSO that can be used in embodiments of the exosome mixtures of the present disclosure are acetone, DMF (N,N-dimethylformamide), acetonitrile, HMF (hydroxymethylfurfural), crown ethers, fatty acids, essential oils, urea, azone, sodium PCA, mixtures thereof etc.

Epsilon-poly-L-lysine (ε-PL) is a natural antimicrobial cationic peptide and is the preferable preservative in exosome mixture embodiments of the present disclosure. ε-PL can be present in embodiments of the present disclosure in an amount of about 0.015 wt % to about 0.035 wt %, about 0.025 wt %. Linatural is a combination of propylene glycol, potassium sorbate, and ethylhexyl glycerin and has been widely used in the cosmetic industry. Linatural can be present in embodiments of the exosome mixtures of the present disclosure in an amount of about 0.5 wt % to about 2.0 wt %. Phenoxyethanol is a preservative used in many cosmetics and personal care products. Phenoxyethanol can be present in exosome mixture embodiments of the present disclosure in an amount of about 0.001 wt % to about 1.00 wt %.

Other examples of a preservative that can be used in exosome mixture embodiments of the present disclosure are K sorbate, aminobenzoate esters, quaternary ammonium cations and/or compounds, (BZK), benzoic acid/salts, benzyl alcohol, chlorhexidine, chlorocresol, imidurea, bronopol, propionic acid/salts, sorbic acid/salts, phenol, acetate, borates, nitrates, or mixtures thereof etc. The amount of these preservatives should be no more than about 0.015 wt %.

Embodiments of the present disclosure also include bone graft therapeutic compositions including bone or other material to be used for bone grafts and exosome mixtures of the present disclosure as well as the methods of making and using/treating using such therapeutic compositions. The natural bone material used for the compositions of the present disclosure can be fresh or frozen, freeze-dried or demineralized freeze-dried (e.g., decalcified freeze-dried bone). The grafting material for the compositions of the present disclosure can be material derived from natural bone material such as, for example, cadaveric sources (allograft), derived from animal sources (xenograft) or derived from the patient (autogenous) or derived from non-bone, but otherwise natural or man-made sources (alloplast—a type of glass made from a naturally occurring mineral in bone called hydroxyapatite).

Artificial bone for alloplast bone grafts can be created from natural or man-made bone substitute materials including, for example, ceramics such as calcium phosphates (e.g., hydroxyapatite and tricalcium phosphate), calcium sodium phosphosilicate (Bioglass®) and calcium sulfate; all of which are biologically active to different degrees depending on solubility in the physiological environment. These materials can be doped with growth factors, ions such as strontium or mixed with bone marrow aspirate to increase biological activity. The presence of elements such as strontium can result in higher bone mineral density and enhanced osteoblast proliferation in vivo.

Embodiments of the exosome mixtures of the present disclosure include exosomes (for example, exosomes obtained or extracted from placental cells and stem cells) in an amount of about 0.25 wt % to about 1.00 wt %, about 50 wt % or about 10 million to about 20 trillion exosomes per 1 ml volume in the exosome mixture and fresh or frozen bone material, freeze-dried bone material, demineralized freeze-dried bone material (e.g., decalcified freeze-dried bone), other natural or man-made bone substitute materials or a mixture of any two in an total amount of bone material of about 0.1 gram to about 10.0 grams. In embodiments of the present disclosure, about 40 wt % to about 60 wt %, about 50 wt % to about 50 wt % (e.g., about 1 cc alloplast to about 1 cc exosome mixture), about 60 wt % to about 40 wt % for packing a hole from where a tooth was extracted; about 25 wt % to about 75 wt %, about 33.3 wt % to about 66.6 wt % (e.g., about 1 cc alloplast to about 2 cc exosome liquid), about 75 wt % to about 25 wt % for packing around a tooth or implant to promote bone growth, and about 30 wt % to about 70 wt %, about 40 wt % to about 60 wt % (e.g., about 2 cc alloplast to about 4 cc exosome liquid), about 70 wt % to about 30 wt % for sinus floor Elevation Regeneration. The exosome mixture composition prior to being mixed with the natural or man-made bone can be a liquid composition or kept in a frozen state which is thawed before being mixed with the natural or man-made bone material. The liquid version of the exosome mixture composition prior to being mixed with the natural or man-made bone includes sterile 0.9 wt % saline, phosphate buffered saline, or HEPES buffer solution. etc.

A bone graft is a surgical procedure used to fix problems with bones or joints. Bone grafting is beneficial in fixing bones that are damaged from trauma or problem joints. It's also useful for growing bone around an implanted device, such as a total knee replacement where there is bone loss or a fracture. A bone graft may fill an area where bone is absent or help provide additional structural stability by growing additional bone around or in conjunction with already existing bone tissue.

Methods included in the present disclosure include application of bone graft compositions of the present disclosure in bone grafts involving various applications including, for example, dental applications and orthopedic applications. In general, the bone graft therapeutic compositions (e.g., bone or other material to be used for bone grafts and exosomes) are applied to an area of bone tissue or an areas adjacent bone tissue where bone growth is desired. The bone graft therapeutic composition acts as a scaffold for new bone growth and, thereby, extending or strengthening the adjacent bone tissue.

In general, dental applications can include use of bone grafting in the application of dental implants to restore the edentulous area of a missing tooth. Dental implants may require bones underneath them for support and proper integration into the mouth. Bone grafts can be also used prior to implant placement or simultaneously therewith. People who have been edentulous (without teeth) for a prolonged period may not have enough bone left in the necessary locations. In such a case, autologous bone can be taken from the chin, from the pilot holes for the implants, or even from the iliac crest of the pelvis and inserted into the mouth underneath the new implant using an appropriate bone graft therapeutic composition of the present disclosure. Alternatively, exogenous bone can be used: xenograft is the most commonly used, because it offers the advantage of exceptional volume stability over time.

Another common bone graft in orthopedic applications an include those used for the fibular shaft. After a segment of the fibular shaft has been removed normal activities, such as running and jumping are not permitted on the leg with the bone deficit. The grafted, vascularized fibulas have been used to restore skeletal integrity to long bones of limbs in which congenital bone defects exist and to replace segments of bone after trauma or malignant tumor invasion.

Allografts are commonly used in hip, knee, or long bone reconstruction. Long bones include arms and legs. The advantage is that no additional surgery is needed to acquire the bone. It also lowers your risk of infection since additional incisions or surgery aren't required. Allograft bone transplant involves bone that has no living cells so that the risk of rejection is minimal as opposed to organ transplants, in which living cells are present. Since the transplanted bone doesn't contain living marrow, there is no need to match blood types between the donor and the recipient.

Spinal fusion is a very common back and neck surgery. In simplest terms, the goal of a spinal fusion is to fuse 2 spinal bones (vertebrae) together, creating one solid bone and restoring spinal stability or restoring alignment. Mechanical devices like rods and screws can be used to stabilize the fused vertebrae. These screws are attached to metal plates or metal rods that are bolted together in the back of the spine. This combination of hardware creates a solid "brace" that holds the vertebrae in place. These devices are intended to stop movement from occurring between the vertebrae that are being fused, allowing a solid fusion to occur. To stimulate the bone fusion, a spine surgeon will use additional bone called bone graft. This graft material is necessary to "trick" the body into causing living bone to cross the gap and join to the other side.

Stem-Cell exosomes are extra-cellular vesicles that are secreted by mesenchymal stem cells into the cell culture medium. They typically range in size from 30 nm-150 nm. The exosomes themselves contain a variety of microRNAs (miRNA), cytokines, and growth factors. Exosomes have the ability to fuse with other cells of the human body and release their content directly into the merging cell. Therefore, no uptake mechanisms for these exosomes are necessary in order for them to fuse with a target cell.

Together with the exosomes, stem cells also secret cytokines, growth factors and a multitude of other proteins and peptides directly into the surrounding culture medium. In general, the entirety of all molecules released by stem cells can be summarized as "secretome". Depending on the method of culture medium collection and refinement, the composition of the final product can be comprised of pure exosomes or a preparation that contains exosomes, and all stem cell secreted molecules like cytokines, growth factors and proteins. The exact composition of the "secretome" varies and depends on the stem cell type/origin, culture conditions, and methods of concentration and buffer exchange.

For bone graft compositions of the present disclosure, the final bone graft composition needs to be sterile and free of endotoxins if the product is intended for injection into humans. In order to meet these conditions, the cell culture needs to be performed under aseptic conditions throughout the production (i.e., from receiving of placental tissue, stem cell isolation, culturing and exosome extraction) as there is no FDA approved final sterilization step for this biologic. Traditional final sterilization through autoclaving, gamma radiation or other methods would destroy the exosomes and the contained miRNA, cytokines and proteins. Therefore, in order to sterilize such exosomes for use in the bone graft compositions of the present disclosure, the procedure that can be used are via refrigerated ultracentrifugation, and/or vacuum filter sterilization, and/or immunoisolation (immunoprecipitate) of exosomes (e.g., Mesenchymal Stem Cell Derived Exosomes The Potential for Translational Nanomedicine (2015) Chapter 6—Current Methods to Purify And Characterize Exosomes pages 63-92).

The content of exosomes and the surrounding medium is comprised of miRNA, cytokines, growth factors, proteins/enzymes, peptides and other compounds. These molecules can exert a variety of beneficial effects at the target site. These can include anti-inflammatory, antifibrotic, antiapoptotic, proangiogenic, and immunomodulatory effects. Depending on stem cell growth conditions, the composition of the exosomes and secretome can be guided toward specific effects. The exact stimulation and its effects can include culturing under hypoxic conditions or the addition of inflammatory cytokines to the growth medium to stimulate anti-inflammatory responses that are represented in the secretome composition. As a result, culturing conditions and preparation of the final medium will greatly influence the potential beneficial effects of the stem cell exosomes and secretomes.

A pure exosome product (e.g., stem cell exosomes), such as one that can be used in the mixtures, compositions and methods of the present disclosure can be obtained by precipitation, wash, and resuspension of exosomes in various biological buffers or saline solutions that support the stability of the exosomes. This results in a pure exosome product that is free of any other components of the secretome. A second way of pure exosome preparation is ultracentrifugation. Here, an exosome rich medium is centrifuged at various speeds to first remove cell debris and other, larger vesicles. Finally, the preparation is centrifuged at high speed, typically around 100,000× g (gravity). Over time, the exosomes will precipitate and can then be washed and resuspended in the desired buffer or medium.

Stem cell secretome preparations contain the exosomes as well as all stem-cell secreted soluble free molecules such as cytokines, proteins, peptides and growth factors. Here, the stem cell culture medium liquid (conditioned medium) is removed by dialysis which retains all molecules and exosomes based on the chosen pore size of the dialysis membrane. The removed medium is then replaced by the desired target matrix, e.g., 0.9 wt % saline or phosphate buffered saline. Larger microvesicles, typically larger than 200 nm, can be removed from the final product using various additional filtration processes.

For bone graft compositions of the present disclosure, the exosomes, such as those included in the exosome mixtures of the present disclosure as well as the bone graft compositions and method of the present disclosure, sterile 0.9 wt % saline is preferred. For topical applications, different buffers can be used, e.g., phosphate buffered saline, HEPES buffer etc. In general, Ph values should range between 5-7. However, Ph values in the lower range (Ph 3-5) or higher range (Ph 7-9) may activate or deactivate specific proteins which might be preferred for targeted applications.

Dialysis of filtration of conditioned medium results in a concentrated secretome product which contains exosomes and most other components secreted by stem cells. The composition strongly depends on the pore size of the filtration membrane which determines the molecule size that is retained within the solution.

The maximum number of exosomes per milliliter (Ml) can exceed tens of trillions per MI but generally is around 10 million to about 20 trillion per MI in the exosome mixture for a finished product.

Other optional ingredients in addition to the bone or other material to be used for bone grafts and the exosome components of the present disclosure includes but not limited to, for example, a stretched polytetrafluoroethylene membrane (e.g., Gore-Tex® (a highly durable, breathable, waterproof and windproof fabric) and a bovine resorbable collagen membrane. The stretched polytetrafluoroethylene membrane, for example, can be used as a "band aid" or barrier in which after tooth extraction, the hole formed when the tooth was extracted is packed with the exosome-alloplast paste, then the stretched polytetrafluoroethylene membrane is used to cover the hole similar to using a band aid to cover a cut. The bovine collagen membrane is used similarly, just like band aid).

The embodiments of the present disclosure including exosome mixtures can be made at about room temperature by combining the above described exosome suspensions in approximately isotonic aqueous solutions of, for example, 0.9 wt % sodium or phosphate buffered saline with a solvent/skin penetrant (e.g., DMSO) and preservative (e.g., epsilon poly L-lysine). Additional water at about room temperature can be added (isotonic or distilled) to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

The embodiments of the present disclosure including exosomes and liposomes and/or niosomes where it is desired to have liposomes and/or niosomes with exosomes included therein can be made at about room temperature by combining the above described exosome suspensions in approximately isotonic aqueous solutions of, for example, 0.9 wt % sodium or phosphate buffered saline with at least one lipid to form the liposomes and/or niosomes (e.g., lecithin). Then DMSO and preservative (e.g., epsilon poly L-lysine) are added at about room temperature. Additional water can be added at about room temperature (isotonic or distilled) to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

The embodiments of the present disclosure including exosomes and liposomes and/or niosomes where it is desired to have the exosomes external to the liposomes and/or niosomes can be made at about room temperature by adding at least one a lipid to water to form the liposomes and/or niosomes (e.g., lecithin). Then DMSO and preservative (e.g., epsilon poly L-lysine) are added at about room temperature. The above described exosome suspensions in approximately isotonic aqueous solutions of, for example, 0.9 wt % sodium or phosphate buffered saline can be added at about room temperature. Additional water can be added (isotonic or distilled) at about room temperature to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

The embodiments of the present disclosure including exosomes and liposomes and/or niosomes where it is desired to have some exosomes external to the liposomes and/or niosomes and liposomes and/or niosomes with some exosomes included therein can be made at about room temperature by combining a portion of the above described exosome suspensions in approximately isotonic aqueous solutions of, for example, 0.9 wt % sodium or phosphate buffered saline with at least one lipid to form the liposomes and/or niosomes (e.g., lecithin). Then DMSO and preservative (e.g., epsilon poly L-lysine) are added at about room temperature. Another portion of the above described exosome suspensions in approximately isotonic aqueous solutions of, for example, 0.9 wt % sodium or phosphate buffered saline can then be added at about room temperature. Additional water can be added (isotonic or distilled) at about room temperature to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

Example 1—Exemplified Exosome-Containing Mixture

| Item # | Ingredient | Function | wt % in Example | Approximate lower wt % amount acceptable | Approximate upper wt % amount acceptable |
|---|---|---|---|---|---|
| 1 | Water | Solvent | 87.45 | 60.00 | 90.00 |
| 2 | Lecithin | Phospholipid | 11.00 | 1.00 | 20.00 |
| 3 | ε-polyl-l-lysine | Preservative | 0.05 | 0.00 | 0.50 |
| 4 | DMSO | Solvent | 0.50 | 0.01 | 2.00 |
| 5 | Exosome | Active | 1.00 | 0.01 | 5.00 |
|   |   | Total | 100.00 |   |   |

Example 2—Exemplified Method of Making the Exosome-Containing Mixture

1. Lecithin is mixed with 40 wt % water until homogenous.
2. QS remaining water to mixture and add ε-polyl-l-lysine and DMSO. Additionally, buffers such as ammonium sulfate, sodium citrate, sodium chloride, sodium acetate could be added to maintain a pH between about 5 to about 7.
3. Exosomes are then added last to the mixture to form a mixture where the exosome is outside the liposome.

Example 3—Exemplified Method of Making the Exosome-Containing Mixture

1. Lecithin is mixed with 40 wt % water and the exosomes until homogenous.
2. QS remaining water to mixture and add ε-polyl-l-lysine, Additionally, buffers such as ammonium sulfate, sodium citrate, sodium chloride, sodium acetate could be added to maintain a pH between about 5 to about 7.
3. After the addition of the last component, the mixture is heated to about 65° C. to about 75° C. for 30 minutes to sterilize as needed and quickly cooled to about 10° C. to about 22° C.

Since the exosomes are added to the Lecithin mixture at the beginning of the process, the exosome is inside the liposome. However, if exosomes are added at the end of the process, the exosome will be outside the liposome. This is also acceptable.

Example 4—Exemplified Post Extract Augmentations Procedure and Study

Design: 1, 2, 3, and 4-month x-ray or CT scan analysis
Strength: 200 million exosomes per cc
Dose: 1 cc alloplast
  1 cc Exosome solution
Subjects: 5 patients; males and/or non-pregnant, non-lactating females, general population with intra-oral and radiographic or CT scan evidence to support decision to extract the tooth.

The dosage form is referred to as a alloplast-Exosome paste mixture and includes products that may be described elsewhere or known as Allografts or grafts. The alloplast-Exosome mixture ratio should all be accurately weighed. This above starting ratio is used for mandibular (jaw) extractions. This is the most concentrated of the ratios.

Packing the cavity is easier due to gravity. Additionally, saliva and other fluids will further "wet" the mixture after packing. Depending on the patient, some salivate, some have dry mouth, the dentist will add or lessen the exosome solution accordingly. Exosomes are harvested from human umbilical cord derived mesenchymal stem cells. Umbilical cord is collected with informed consent from disease-free donors with normal pregnancy. Mesenchymal stem cells are isolated, cells are expanded and then seeded into a bioreactor. Conditioned culture medium is harvested from the bioreactor and exosomes are extracted, characterized and diluted to the required concentration with sterile 0.9 wt % saline. The finished product is tested for sterility and endotoxins by an independent laboratory before used in the procedures.

After tooth extraction, the alloplast-exosome mixture (graft) will be applied and is gently packed into the site, a disc of collagen plug will be used and placed over the site containing the graft. The plug should be secured with a suture. The graft material should fill the existing socket and the site will be allowed to heal for up to 4 months, while x-ray or CT-scans should be conducted at the 1-, 2-, 3- and 4-month time points. The strength of this alloplast-exosome mixture is based upon the number of exosomes in the serum, expressed as a number based upon volume. The strength of the whole mixture is influenced by the volume surface area of the maxillary/mandibular cavity, the exosome concentration, and amount of alloplast used.

Example 5—Exemplified Regenerative Amount of Bone with Natural Teeth Procedure and Study Design: 1, 2, 3, and 4-month x-ray or CT scan analysis
Strength: 200 million exosomes per cc
  Dose: 1 cc alloplast
  2 cc Exosome solution
  Subjects: 5 patients; males and/or non-pregnant, non-lactating females, general population with intra-oral and radiographic or CT scan evidence to support decision to treat the site.

The dosage form is referred to as a alloplast-exosome paste mixture and includes products that may be described elsewhere or known as Allografts or grafts. The alloplast-Exosome mixture ratio should all be accurately weighed. The starting ratio used is 1 cc alloplast:2 cc exosome solution. This procedure is done by cutting the gum and applying the paste around the teeth to grow additional bone to support existing teeth or implants. The gums are then sutured back. This is done when bone on both mandible or maxilla have receded that there's not enough bone to support the existing tooth/implant. The surgeon will adjust the ratio accordingly depending on the patient's mouth status (salivate or dry mouth). Exosomes are harvested from human umbilical cord derived mesenchymal stem cells. Umbilical cord is collected with informed consent from disease-free donors with normal pregnancy. Mesenchymal stem cells are isolated, cells are expanded and then seeded into a bioreactor. Conditioned culture medium is harvested from the bioreactor and exosomes are extracted, characterized and diluted to the required concentration with sterile 0.9 wt % saline. The finished product is tested for sterility and endotoxins by an independent laboratory before used in the procedures.

For regenerative amount of bone with natural teeth, after an incision in the gum tissue is made, the alloplast-exosome paste will be applied on the root of teeth after complete decontamination using scaling and root planning or tetracycline. A picture/x-ray, CT-scan of the wound, severity, color, should be taken at the beginning of the study and at the 1-, 2-, 3- and 4-month time points. A qualified professional should examine the wound before, during, and after the study. The amount of attachment could be measured using a dental probe. The strength of this alloplast-exosome mixture is based upon the number of exosomes in the serum, expressed as a number based upon volume. The strength of the whole mixture is influenced by the volume surface area of the maxillary/mandibular cavity, the exosome concentration, and amount of alloplast used.

Example 6—Exemplified Regenerative Amount of Bone with Tooth Implant Procedure and Study Design: 1, 2, 3, and 4-month x-ray or CT scan analysis
Strength: 200 million exosomes per cc
  Dose: 1 cc alloplast
  2 cc Exosome solution
  Subjects: 5 patients; males and/or non-pregnant, non-lactating females, general population with intra-oral and radiographic or CT scan evidence to support decision to treat the site.

The dosage form is referred to as a alloplast-exosome paste mixture and includes products that may be described elsewhere or known as Allografts or grafts. The alloplast-Exosome mixture ratio should all be accurately weighed. The starting ratio used is 1 cc alloplast:2 cc exosome solution. This procedure is done by cutting the gum and applying the paste around the teeth to grow additional bone to support existing teeth or implants. The gums are then sutured back. This is done when bone on both mandible or maxilla have receded that there's not enough bone to support the existing tooth/implant. The surgeon will adjust the ratio accordingly depending on the patient's mouth status (salivate or dry mouth). Exosomes are harvested from human umbilical cord derived mesenchymal stem cells. Umbilical cord is collected with informed consent from disease-free donors with normal pregnancy. Mesenchymal stem cells are isolated, cells are expanded and then seeded into a bioreactor. Conditioned culture medium is harvested from the bioreactor and exosomes are extracted, characterized and diluted to the required concentration with sterile 0.9 wt % saline. The finished product is tested for sterility and endotoxins by an independent laboratory before used in the procedures.

For implant, the alloplast-exosome paste will be applied on the endosseous implant surface or exposed implant surface after insertion of the implant. A picture/x-ray, CT-scan of the wound, severity, color, should be taken at the beginning of the study and at the 1-, 2-, 3- and 4-month time points. A qualified professional should examine the wound before, during, and after the study. The strength of this alloplast-exosome mixture is based upon the number of exosomes in the serum, expressed as a number based upon volume. The strength of the whole mixture is influenced by the volume surface area of the maxillary/mandibular cavity, the exosome concentration, and amount of alloplast used.

Example 7—Exemplified Maxillary Sinus Floor Elevation Regeneration Procedure and Study Design: 1, 2, 3, and 4-month x-ray or CT scan analysis
Strength: 200 million exosomes per cc
  Dose: 4 cc alloplast
  6 cc Exosome solution Subjects: 5 patients; males and/or non-pregnant, non-lactating females, general population with intra-oral and radiographic or CT scan evidence to support decision to extract the tooth and treat the area.

The dosage form is referred to as a alloplast-exosome paste mixture and includes products that may be described elsewhere or known as Allografts or grafts. The alloplast-exosome mixture ratio should all be accurately weighed. The starting ratio is 4 cc alloplast:6 cc exosome solution (2:3 ratio). This starting ratio of a higher exosome solution to alloplast is due to the dryness of the sinus cavity . . . more liquid is needed up there unlike the mouth where saliva is constantly wetting the area. The surgeon can start with a 2 cc:3 cc ratio if the patient has a smaller sinus cavity, but the majority will use 4 cc:6 cc ratio. Once the bone graft sets and becomes bone, then the upper implant will have something to anchor to. Exosomes are harvested from human umbilical cord derived mesenchymal stem cells. Umbilical cord is collected with informed consent from disease-free donors with normal pregnancy. Mesenchymal stem cells are isolated, cells are expanded and then seeded into a bioreactor. Conditioned culture medium is harvested from the bioreactor and exosomes are extracted, characterized and diluted to the required concentration with sterile 0.9 wt % saline. The finished product is tested for sterility and endotoxins by an independent laboratory before used in the procedures.

Figure 1A:
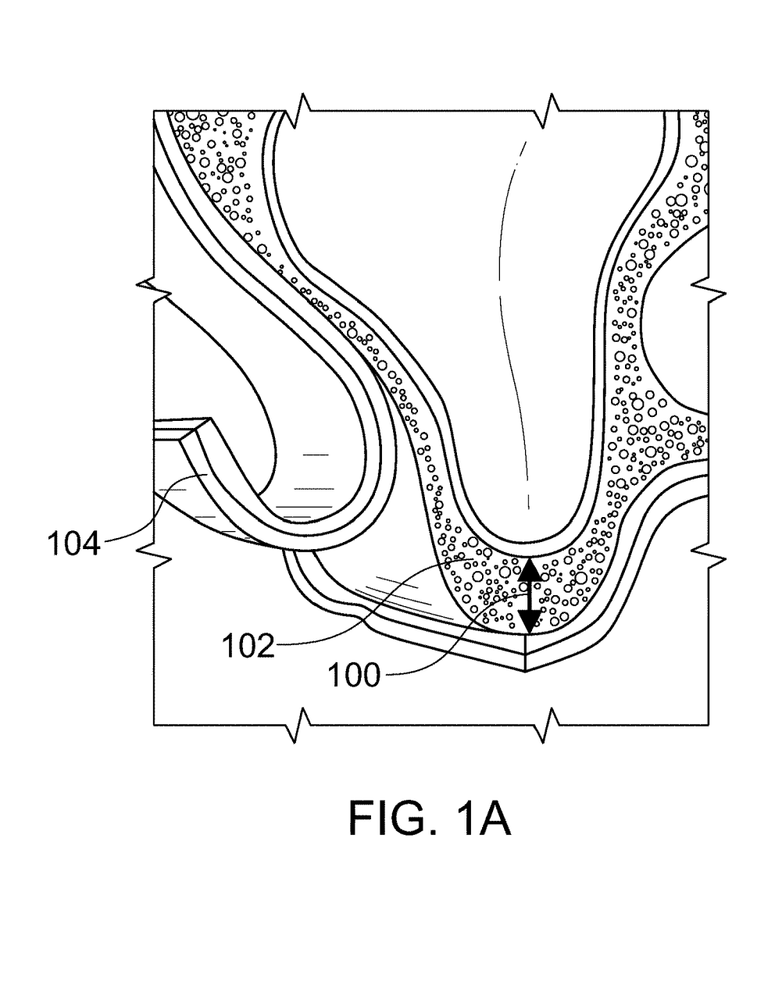
FIGS. 1A to 1F is a schematic illustration of a maxillary sinus floor augmentation.
Figure 1B:
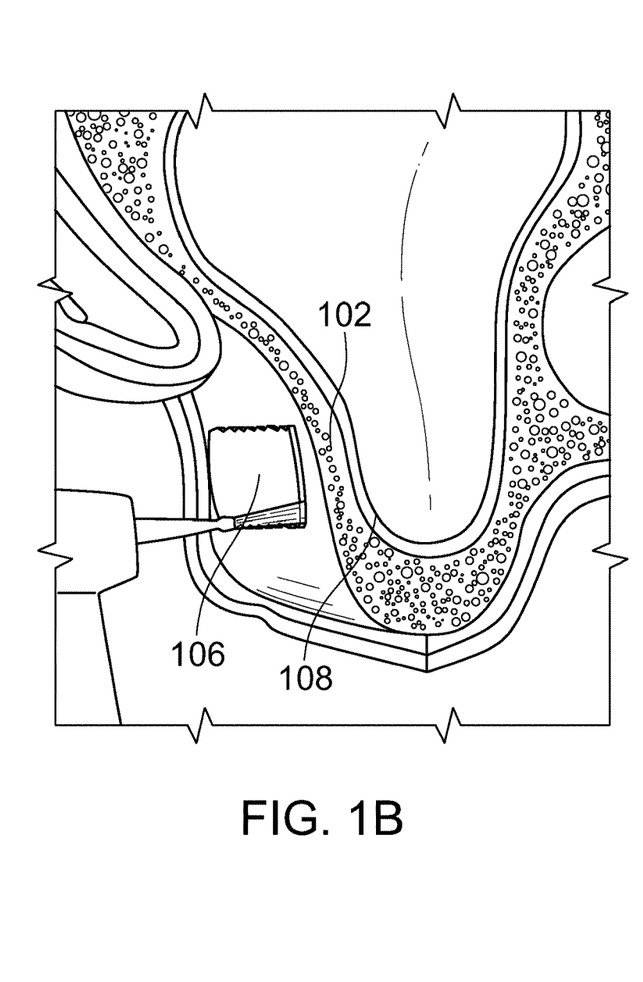
Figure 1C:
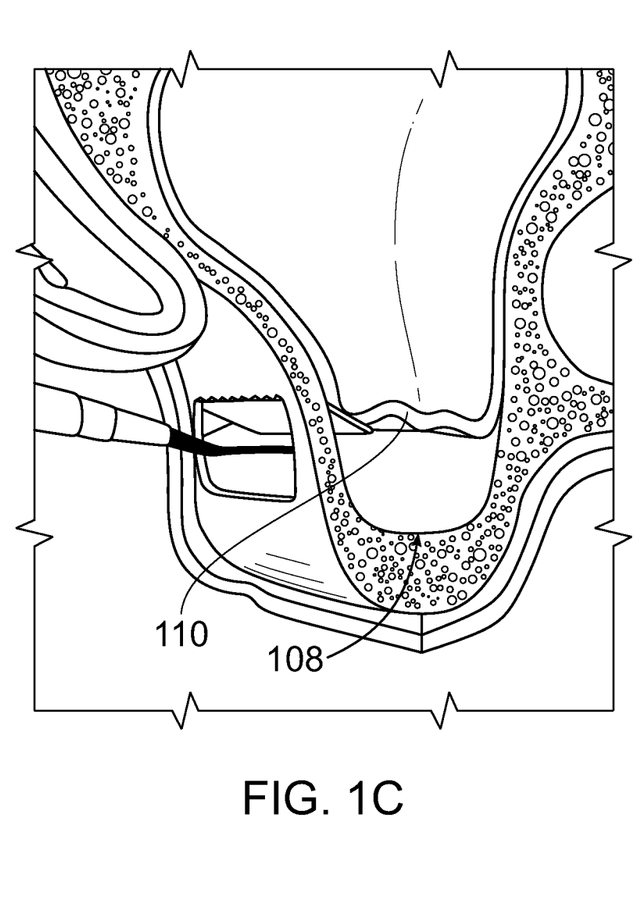
Figure 1D:
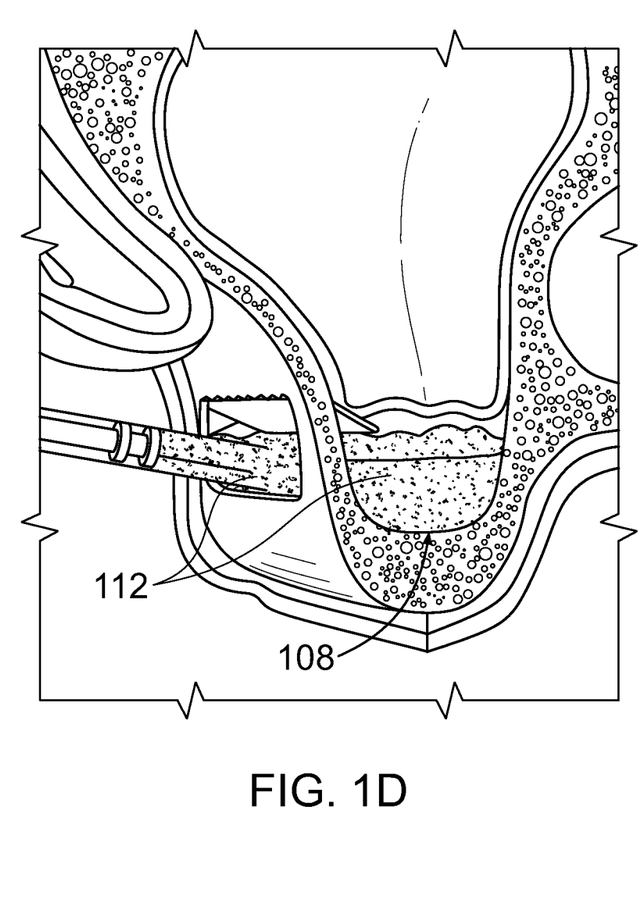
Figure 1E:
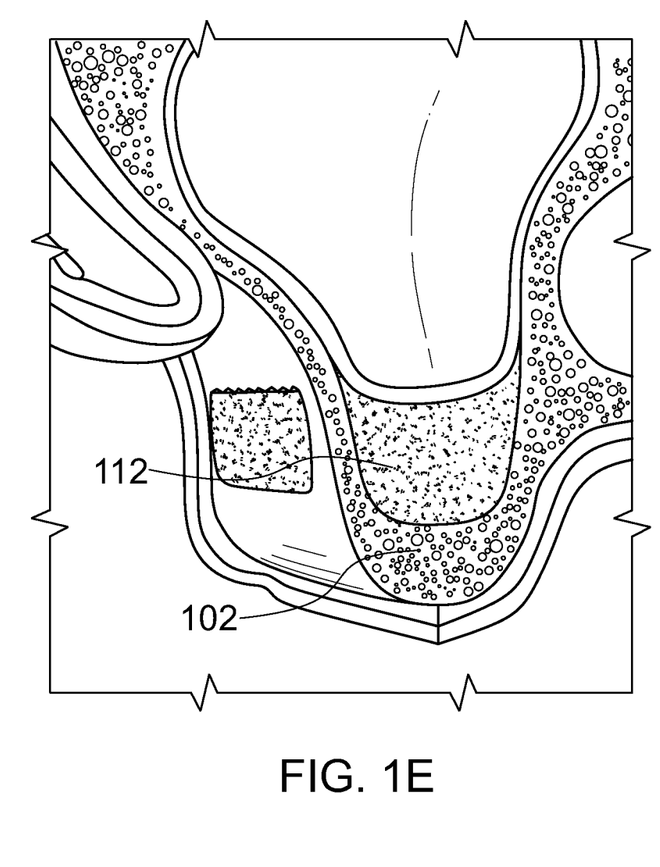
Figure 1F:
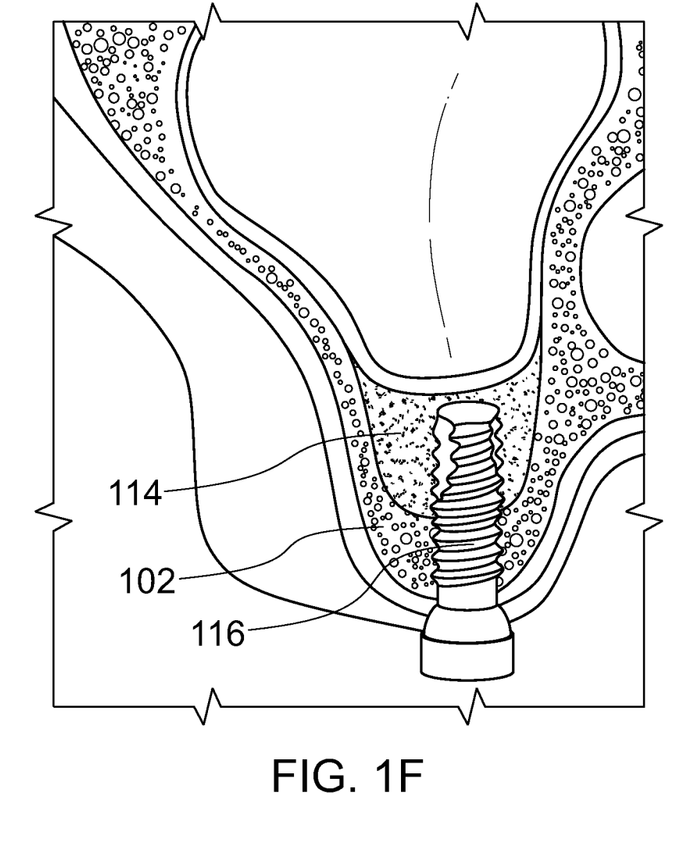

In one embodiment, for maxillary sinus floor augmentation, a Caldwell-Luc intra-oral approach is used in FIGS. 1A to 1F. In FIG. 1A, there is insufficient height 100 in the bone tissue 102 to support a tooth implant. After gum tissue 104 is pealed back, a window 106 is cut laterally in shown in FIG. 1B to expose bone tissue 102 adjacent the lateral wall of sinus 108. The Schneiderian membrane 110 is accessed and lifted intact apically in FIG. 1C. In FIGS. 1D and 1E, the alloplast-exosome mixture 112 is added to the floor of the sinus 108 and compacted prior to suturing. As shown in FIG. 1F, after the window has been sutured closed and bone graft has generated sufficient additional bone mass 114 along with bone tissue 102, there is greater bone mass and a support 116 for the tooth implant can be inserted. The strength of this alloplast-exosome mixture is based upon the number of exosomes in the serum, expressed as a number based upon volume. The strength of the whole mixture is influenced by the volume surface area of the maxillary/mandibular cavity, the exosome concentration, and amount of alloplast used. this procedure is needed when bone is added inside the sinus after lifting the Schneiderian membrane prior to implant placement. This is done when sinuses are too low and not enough bone available for conventional implant placement. Because it's difficult to pack the maxillary site upside down (unlike the jaw where gravity keeps the bone powder down) you need to pack the site from above and the only way is to cut a hole into the upper sinus and pack it from above i.e., maxillary sinus floor.

Example 8—Exemplified Implant Placement in Conjunction with Bone Graft Study

Design: 1, 2, 3, and 4-month x-ray or CT scan analysis
Strength: 200 million exosomes per cc
  Dose: 1 cc alloplast
  1 cc Exosome solution
  Subjects: 5 patients; males and/or non-pregnant, non-lactating females, general population with intra-oral and radiographic or CT scan evidence to support decision to extract the tooth.

The dosage form is referred to as a alloplast-exosome paste mixture and includes products that may be described elsewhere or known as Allografts or grafts. The alloplast-Exosome mixture ratio should all be accurately weighed. Exosomes are harvested from human umbilical cord derived mesenchymal stem cells. Umbilical cord is collected with informed consent from disease-free donors with normal pregnancy. Mesenchymal stem cells are isolated, cells are expanded and then seeded into a bioreactor. Conditioned culture medium is harvested from the bioreactor and exosomes are extracted, characterized and diluted to the required concentration with sterile 0.9 wt % saline. The finished product is tested for sterility and endotoxins by an independent laboratory before used in the procedures.

For implant, the alloplast-exosome paste will be applied on the endosseous implant surface or exposed implant surface after insertion of the implant. A picture/x-ray, CT-scan of the wound, severity, color, should be taken at the beginning of the study and at the 1-, 2-, 3- and 4-month time points. A qualified professional should examine the wound before, during, and after the study. The strength of this alloplast-exosome mixture is based upon the number of exosomes in the serum, expressed as a number based upon volume. The strength of the whole mixture is influenced by the volume surface area of the maxillary/mandibular cavity, the exosome concentration, and amount of alloplast used.

For the above exemplified procedures and other similar procedures related to compositions and methods of the present disclosure, for post extract augmentation, and implant placement: the ratio used is 1 cc alloplast:1 cc exosome solution. This starting ratio is used for mandibular (jaw) extractions. This is the most concentrated of the ratios. Packing the cavity is easier due to gravity. Additionally, saliva and other fluids will further "wet" the mixture after packing. Depending on the patient, some salivate, some have dry mouth, the dentist will add or lessen the exosome solution accordingly . . . but starting is 1 cc:1 cc.

For the above exemplified procedures and other similar procedures related to compositions and methods of the present disclosure, for regenerative amount of bone with natural or tooth implant, the starting ratio used is 1 cc alloplast:2 cc exosome solution. This procedure is done by cutting the gum and applying the paste around the teeth to grow additional bone to support existing teeth or implants. The gums are then sutured back. This is done when bone on both mandible or maxilla have receded that there's not enough bone to support the existing tooth/implant. The surgeon will adjust the ratio accordingly depending on the patient's mouth status (salivate or dry mouth).

For the above exemplified procedures and other similar procedures related to compositions and methods of the present disclosure, for maxillary sinus floor elevation regeneration: the starting ratio is 4 cc alloplast:6 cc exosome solution (2:3 ratio). This starting ratio of a higher exosome solution to alloplast is due to the dryness of the sinus cavity . . . more liquid is needed up there unlike the mouth where saliva is constantly wetting the area. The surgeon can start with a 2 cc:3 cc ratio if the patient has a smaller sinus cavity, but the majority will use 4 cc:6 cc ratio. Once the bone graft sets and becomes bone, then the upper implant will have something to anchor to.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A bone graft material consisting essentially of bone material, a stem cell exosome mixture, dimethyl sulfoxide and epsilon poly L-lysine.

2. The bone graft material of claim 1, wherein the bone material is selected from the group consisting of natural bone material, man-made bone material and a combination thereof.

3. The bone graft material of claim 2, wherein the natural bone material is selected from the group consisting of fresh bone material, frozen bone material, freeze dried bone material, demineralized freeze dried bone material and a combination thereof.

4. The bone graft material of claim 1, wherein the amount of stem cell exosomes is about 5 wt. % to about 95 wt. % of the stem cell exosome mixture.

5. The bone graft material of claim 1, wherein the amount of stem cell exosomes is about 50 wt. % of the stem cell exosome mixture.

6. The bone graft material of claim 1, wherein the amount of stem cell exosomes is about one thousand to about one trillion stem cell exosomes per 1 ml of the stem cell exosome mixture.

7. The bone graft material of claim 1, wherein the amount of dimethyl sulfoxide is about 0.001 wt. % to about 0.50 wt. % of the bone graft material.

8. The bone graft material of claim 1, wherein the amount of epsilon poly L-lysine is about 0.015 wt. % to about 0.035 wt. % of the bone graft material.

9. The bone graft material of claim 1, wherein the pH of the bone graft material ranges from between about 5.0 to about 7.5.

* * * * *